United States Patent [19]
Hofelich et al.

[11] Patent Number: 5,423,609
[45] Date of Patent: Jun. 13, 1995

[54] METHOD AND APPARATUS FOR DETERMINING THE HEAT OF COMBUSTION OF A MATERIAL BASED ON THE HEIGHT OF A DIFFUSIONAL FLAME WITHIN WHICH THE MATERIAL IS BURNED

[75] Inventors: Thomas C. Hofelich; Ing-Feng Hu, both of Midland; William H. Parth, Saginaw, all of Mich.

[73] Assignee: The Dow Chemical Company, Midland, Mich.

[21] Appl. No.: 181,683

[22] Filed: Jan. 14, 1994

[51] Int. Cl.[6] .................................. G01N 25/22
[52] U.S. Cl. ............................... 374/36; 374/37
[58] Field of Search .......................... 374/36, 37

[56] References Cited

U.S. PATENT DOCUMENTS

| | | | |
|---|---|---|---|
| 1,205,704 | 11/1916 | Breyer | 374/36 |
| 1,417,635 | 5/1922 | Smith | 374/36 |
| 2,052,181 | 8/1936 | Krogh | 374/36 |
| 2,285,866 | 6/1942 | Markle | 374/36 |
| 2,441,117 | 5/1948 | Wagner | 374/36 |
| 3,701,137 | 10/1972 | Hulsman | 340/578 |
| 4,229,967 | 10/1980 | Kneifel et al. | 374/8 |
| 4,306,451 | 12/1981 | Szonntagh | 374/36 |
| 4,637,735 | 1/1987 | de Ris et al. | 374/37 |
| 5,224,776 | 7/1993 | Clingman, Jr. et al. | 374/37 |

FOREIGN PATENT DOCUMENTS

| | | | |
|---|---|---|---|
| 60-142238 | 7/1985 | Japan | 374/36 |
| 6605207 | 10/1967 | Netherlands | 374/36 |
| 1723510 | 3/1992 | U.S.S.R. | 374/36 |

OTHER PUBLICATIONS

Dictionary of Physics, edited by Valerie Pitt, pp. 282, 311 and 382, Penguin Ltd., England (1987).

*Primary Examiner*—Diego F. F. Gutierrez
*Attorney, Agent, or Firm*—James T. Hoppe

[57] ABSTRACT

An apparatus and method are provided for determining the heat of combustion of a material. The apparatus comprises a burner capable of producing a diffusional flame; a device for conveying a sample of the material to the burner, so that the sample is burned within the diffusional flame; and a mechanism for determining the height of the flame in the burner. The method of the invention comprises forming a diffusional flame; burning a sample of the material within the diffusional flame; determining the height of the diffusional flame which results as the sample is burned; and comparing the height determined when the sample was burned with heights determined when standards were burned, the standards having known values for their heats of combustion.

20 Claims, 2 Drawing Sheets

METHOD AND APPARATUS FOR DETERMINING THE HEAT OF COMBUSTION OF A MATERIAL BASED ON THE HEIGHT OF A DIFFUSIONAL FLAME WITHIN WHICH THE MATERIAL IS BURNED

This invention relates to the measurement the heat of combustion for various samples. More particularly this invention relates to a method and apparatus capable of being placed on-line for determining the heat of combustion of samples.

BACKGROUND OF THE INVENTION

Combustion is a popular method for waste disposal. For complete combustion of gaseous waste, the fuel to air ratio should be optimized. Too little oxygen may result in waste not being completely burned during the residence time of the waste within the combustion chamber and too much oxygen may cause the flame to extinguish if the flame temperature decreases below the flash point. The oxygen demand for a given waste to be burned completely is dependent on the nature of the waste. Widely varying organic materials have vastly different heats of combustion and therefore require different amounts of oxygen for complete combustion.

This presents a serious problem for waste streams whose compositions or concentrations vary in an unpredictable manner. When materials with large heats of combustion are burned, there may not be enough oxygen available for complete combustion. When the heat of combustion of the waste is too low, insufficient heat may be produced to sustain the flame, resulting in flame extinction. Flame outs and incomplete combustion can cause releases of waste into the environment and/or plant shutdowns.

Current methods used in the control of waste combustion typically involve measuring the flame temperature and the oxygen content after burning the waste and then regulating the flow of auxiliary fuel and oxygen source in order to maintain the desired flame temperature and a fixed excess of oxygen. These current methods make adjustments to the flame feed based on measurements taken after combustion of the sample. Thus, changes in the ratio of fuel to air can only be made after the sample for which a change in the feed gas is needed has been burned. These techniques work adequately when the changes in the composition of the wastes are slow, but sudden changes may result either in the flame being extinguished or releases of incompletely burned wastes before the changes in the flame-feed can be made. Because of the large volumes of waste typically burned in an operating incinerator, even a short period of time with an incorrect amount of oxygen could cause significant damage to the environment.

It would therefore be beneficial to provide a calorimeter which could determine the heat of combustion of a small sample of a material before incinerating the bulk of the material. Once the heat of combustion for the small sample is determined then the feed rates of sample, auxiliary fuel and oxygen can be adjusted in the incinerator to ensure complete combustion of the waste.

Current methods of determining the heat of combustion for a sample typically attempt to measure the heat of combustion directly, by measuring the temperature of a flame which results as the sample is burned. The measured heat of combustion therefore depends on the temperature of the flame. However, the temperature of the flame will vary, depending on the size of the flame. This is largely due to the fact that when a large amount of fuel is burned, the flames are thicker giving rise to radiative heat transfer effects. Therefore, a conventional calorimeter in which the sample is burned in a small-scale flame would give a vastly different result than a calorimeter using a larger flame, such as those typically used in large-scale incinerators. Accordingly, conventional calorimeters can not be used with a small amount of sample to give reliable indications of the sample's heat of combustion in an incinerator and so do not reliably indicate the optimum conditions necessary to completely incinerate the waste.

Furthermore, instruments which attempt to measure the heat of the flame directly require the transfer of heat from the flame to the measuring device. Heat transfer in these devices is usually accomplished by conduction. Materials which are typically used to conduct heat are generally not resistant to corrosion. Therefore, it is not practical to use currently available instruments in hostile environments where they quickly become corroded.

One solution to some of the problems associated with attempting to determine heats of combustion using smaller flames was described by John de Ris et al. in U.S. Pat. No. 4,637,735. This reference provides a bench scale apparatus for measuring the heat-release rate of pyrolysis vapors of a material sample. The apparatus contains two sensors: a first to sense the location of the tip of the flame and a second to detect the amount of soot being released from the sample. The amount of soot detected is used to correlate the bench scale test with the large scale flame which would actually be occurring in the incinerator's burner. However, sootiness is not a precise measurement and so does not provide the consistency needed for accurate control of the combustion of waste streams. Furthermore, soot builds up over time, making maintenance of such calorimeters a real concern.

OBJECTIVES OF THE INVENTION

It is therefore an objective of this invention to provide information on the heat of combustion of waste streams before they are burned, allowing the reduction of emissions due to incomplete combustion and reducing auxiliary fuel costs.

It is another objective of the present invention to provide a calorimeter which can be placed on-line so that a greater number of samples can be run, leading to greater control over the combustion.

Yet another objective of the present invention is to provide a calorimeter which is relatively inert so that it can be used in hostile environments without significant corrosion.

It is a further objective of the present invention to provide a calorimeter which includes a sampling system which will allow a flame to be maintained even when the sample to be burned is not combustible.

SUMMARY OF THE INVENTION

In accordance with the present invention, an apparatus and method are provided for determining the heat of combustion of a material. The apparatus comprises a burner means capable of producing a diffusional flame; a means for conveying a sample of the material to the burner means, so that the sample is burned within the diffusional flame; and a means for determining the height of the flame in the burner means.

The method of the invention comprises forming a diffusional flame; burning a sample of the material within the diffusional flame; determining the height of the diffusional flame which results as the sample is burned; and comparing the height determined when the sample was burned with heights determined when standards were burned, the standards having known values for their heats of combustion.

For a more complete understanding of the invention, reference should be made to the Detailed Description of the Invention, which makes reference to the following drawings:

DETAILED DESCRIPTION OF THE INVENTION

The present invention makes use of relationships between flame height, stoichiometric ratios of fuel to air and heats of combustion. Experimentation conducted over 60 years ago demonstrated that the flame height of a diffusional flame is linearly proportional to the stoichiometric ratio of fuel to air, within a given range. S. P. Burke and T. E. W. Schumann, "Laminar Diffusion Flame-Air Entrainment and Burning of Jets of Fuel Gas", *Ind. Eng. Chem.*, 20, 998, (1928). Assuming that the flow rate is constant, the diffusion of oxygen is semi-infinite and the flame is small, the relationship between flame height and the stoichiometric ratio of fuel to air is given by the equation:

$$\text{flame height} = \frac{V(1+i)}{4\pi D}$$

where V is the volume flow rate of the gas being burned, i is the stoichiometric ratio of air to fuel and D is the diffusion coefficient for oxygen. Bernard Lewis and Guenther Von Eble, *Combustion, Flames, and Explosions of Gases*, 2nd ed., pg 481, Academic Press, Inc., 1961. This equation confirms the linear relationship between flame height and stoichiometric ratio of air to fuel.

It has also been shown that the stoichiometric ratio of fuel to air (oxygen) is linearly proportional to the heat of combustion of the compound. See, for example, Lewis and Von Eble, *Combustion, Flamest and Explosions of Gases*, pg 685–689.

Accordingly, the heat of combustion is linearly proportional to the stoichiometric ratio of fuel to air which in turn is linearly proportional to the flame height of a diffusional flame. The present invention uses these principles to determine the heat of combustion of a sample from the height of a diffusional flame formed while burning the sample.

Therefore, in its simplest form, the invention comprises igniting a stream of auxiliary fuel such that a diffusional flame is formed, then directing a sample to the flame so that it is burned within the diffusional flame. The height of the resulting flame is then measured. The heat of combustion for the sample can be determined by comparing the observed flame height to flame heights which resulted from burning one or more standard materials under similar conditions. Thus, a calibration curve (or electronic equivalent) of the standard materials' heat of combustion versus the resultant flame height can be constructed and used to determine the corresponding heat of combustion for a sample, given the flame height which resulted when that sample was burned.

Figure 1:
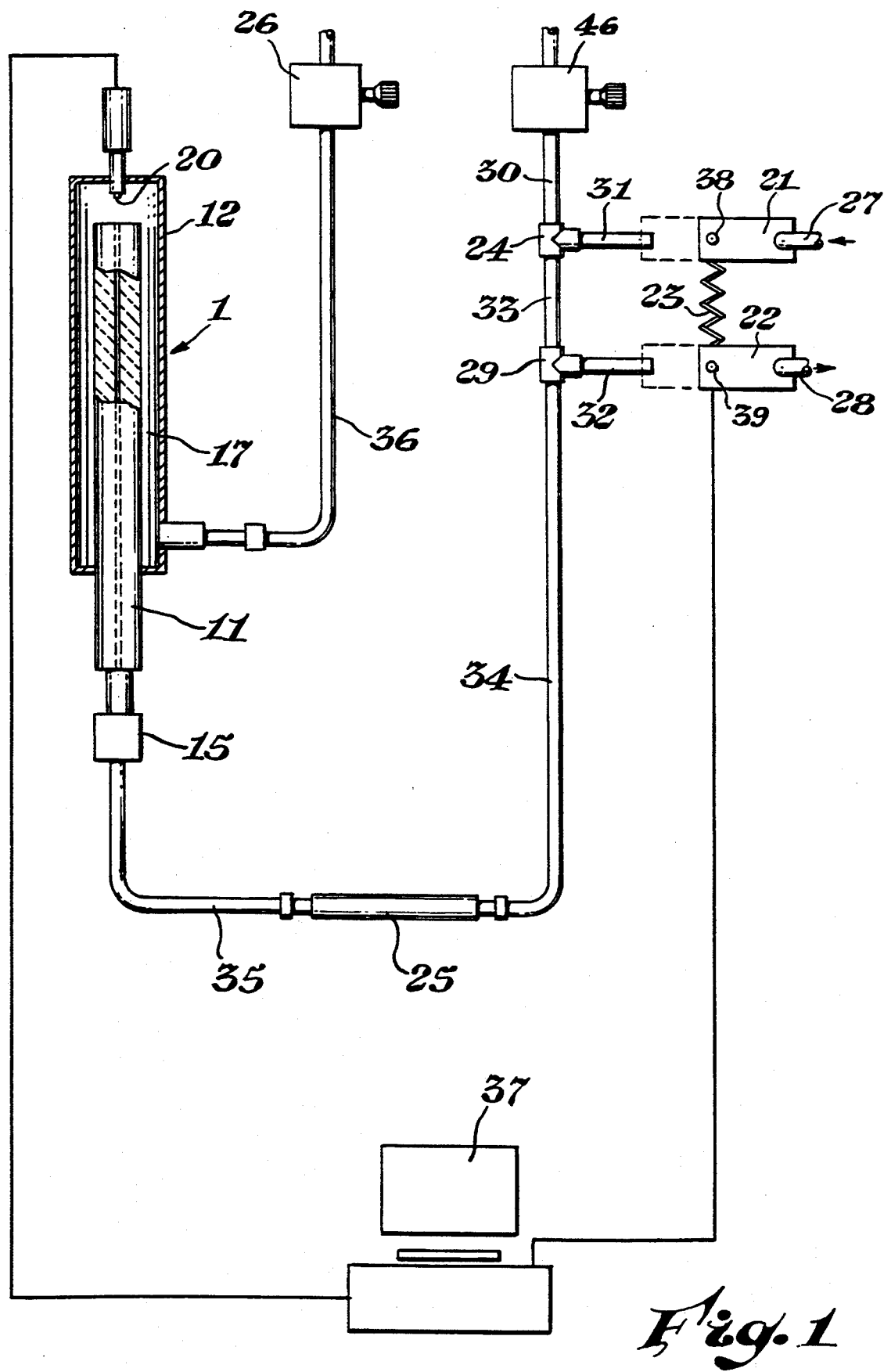
FIG. 1 is a schematic drawing of a preferred arrangement for the apparatus of the invention, showing a diffusional burner with a sampling system.

Referring now to FIG. 1, a schematic of a preferred arrangement for the apparatus of the invention is shown. Generally, the apparatus comprises a diffusional burner 1, a first and a second conduit means 35, 36 leading to the burner, and a means 20 for determining the height of the flame. The first conduit means 35 allows fuel mixed with sample to enter the burner while the second conduit means 36 provides oxygen to the burner.

Any burner capable of producing a diffusional flame will work with this invention. A diffusional flame requires laminar flow of the sample being burned. Laminar flow can be predicted by calculating the Reynolds number for the system. The Reynolds number is given by the following equation as seen in A. G. Gaydon and H. G. Wolfhard, *Flames Their Structure, Radiation and Temperature*, 3d ed., pg. 14, (1970):

$$\text{Reynolds number} = \frac{d_o U_o \rho_o}{\mu_o}$$

where $d_o$ is the burner's nozzle diameter; $U_o$ is the discharge velocity; $\rho_o$ is the density of the sample being burned at 15° C.; and $\mu_o$ is the viscosity of the sample being burned at 15° C. A Reynolds number of less than 2100 is generally indicative of laminar flow. Thus, the nozzle diameter and the discharge velocity of the sample being burned should be optimized to provide a Reynolds number which promotes laminar flow for the intended sample.

Figure 2:
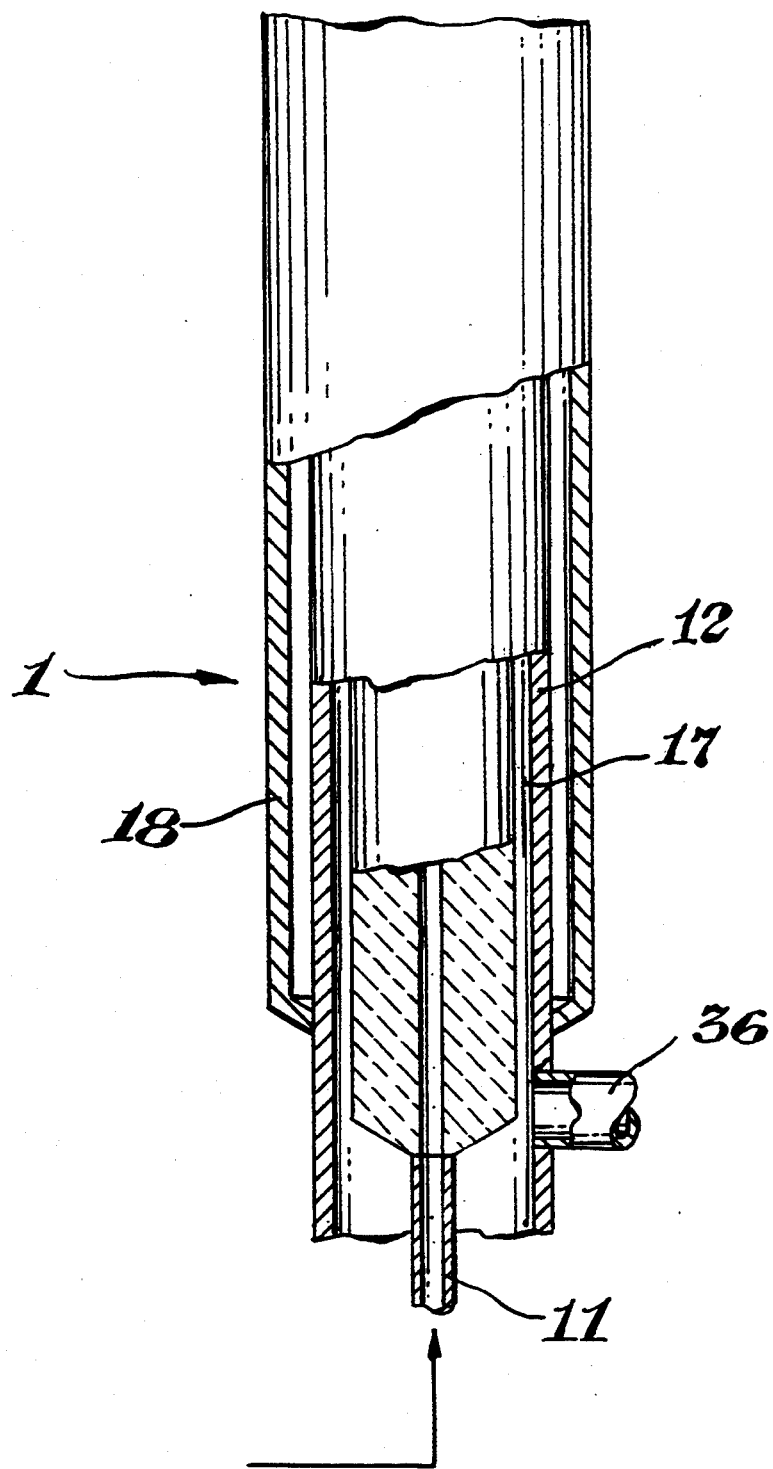
FIG. 2 is a schematic drawing of a burner suitable for use in the invention.

Some suitable burners for use in this invention are discussed in A. G. Gaydon and H. G. Wolfhard, *Flames Their Structure, Radiation and Temperature*, 3d ed., pg. 129–157, (1970). A preferred embodiment of a diffusional burner 1 is depicted in FIG. 2. As shown in that drawing, the burner 1 includes an inner conduit means 11 for delivering fuel into the burner. The inner conduit means 11 is preferably a capillary tube having an inner diameter of approximately 1 mm. The dimensions of the conduit can be varied according to individual needs, but is preferably small enough to encourage laminar flow and to minimize the possibility of flashbacks. Guidance on the prevention of flashbacks can be obtained from "Flame Arresters and Flashback Preventers", Walter B. Howard, *Plant/Operations Progress*, Vol. 1, No. 4, pg 203, (October 1982). Many known materials such as quartz, stainless steel, or HASTELLOY ™ compounds can withstand the elevated temperatures within the burner and can therefore be used to construct the inner conduit 11. Quartz is preferred, however, especially if the calorimeter will be used for analyzing particularly corrosive material.

Coaxially surrounding the inner conduit means 11 is an outer conduit means 12. This outer conduit means 12 is slightly larger in diameter than the inner conduit means 11 providing an annular region 17 between the two conduit means, through which a supply of oxygen is delivered to the interior of the burner. As shown in FIG. 1, the outer conduit means 12 preferably extends downstream past the inner conduit means 11, thereby forming a region where the oxygen source and the fuel/sample can mix through diffusion while still being protected from any turbulent air flow which may be present in the burner. Preferably, the outer conduit means 12 extends several (e.g. 2–4) centimeters past the tip of the flame which results when the auxiliary fuel, flowing at the same flow rate to be used during the analysis, is being burned in the absence of sample. This configuration also prevents the oxygen from diffusing away from the fuel, thereby effectively increasing the concentration of oxygen available to sustain the flame. Like the inner conduit 11, it is preferred that the outer conduit 12 be constructed from quartz, especially when corrosive materials are being analyzed.

It should be appreciated that the above configuration allows the fuel and oxygen source to mix primarily through the diffusion process, such that the Reynolds number for the system will be less than about 2300. The flame will be formed only in the region where oxygen and the fuel are in contact. Consequently, the shape of the flame is dependent on the diffusion process. The flame will continue to be present only until the fuel has been completely burned. Samples with higher heats of combustion will take longer to be completely burned. Longer periods of time translates into higher flames as the fuel travels up from the tip of the inner conduit 11 at a constant rate. Therefore, the heat of combustion of the sample is directly related to the height of the flame.

Additionally, a diffusional burner gives high combustion efficiency and flame stability compared with burners in which the fuel is premixed with oxygen or subjected to turbulence. Furthermore, because this invention allows the height of the flame to be measured rather than measuring the temperature of the flame directly, heat transfer effects are of no concern. Thus, results from a small scale diffusional flame can be readily applied to predict the amount of auxiliary fuel and oxygen required to burn the sample in a full sized incinerator.

Surrounding the inner conduit means 11 and the outer conduit means 12 of the preferred burner depicted in FIG. 2, is an optional chimney means 18, which can further protect the flame from turbulence. The chimney means 18 can also protect the area surrounding the diffusional flame from disturbances so that the heat from the flame will radiate in a uniform manner. This facilitates a non-visual means for measuring the height of the flame, as will be described below. If the means for determining the height of the flame is situated within the outer conduit means 12, then the importance of having a chimney means 18 is greatly diminished.

The chimney means 18 or the outer conduit means 12 also accommodates a means for measuring the height of the flame. Many techniques can be used to determine the flame height including simply providing a window or equivalent which allows an operator to view the flame and physically measure its height. More preferably, optic sensors can be used to automatically determine the flame height.

It is most preferred, however, that the height of the flame be determined from the temperature at a point fixed directly above the diffusional flame. As is known in the art, the temperature of a diffusional flame will not significantly change no matter what fuel is being burned. See for example, Bernard Lewis and Guenther Von Eble, *Combustion, Flames, and Explosions of Gases*, 2nd ed., pg. 705–708. Therefore, as long as the flame is steady and the heat uniformly radiates from the flame, a change in temperature at any given point will be caused only by a change in the shape of the flame. As the flame gets nearer to the point at which the temperature is measured, the temperature of the point increases. If the point at which temperature is measured is located directly above the flame then any change in temperature will be caused only by a change in the height of the diffusional flame. As discussed above, the height of a diffusional flame is directly proportional to the heat of combustion of the fuel which is being burned. Consequently, the temperature at a fixed point located directly above the flame can be correlated to the heat of combustion for the sample which is being burned.

Accordingly, the chimney means 18 preferably allows a means for measuring temperature 20 at a fixed point directly above the flame, as seen in FIG. 1. Even more preferably the means for measuring temperature 20 is located within the outer conduit means 12 as shown in FIG. 1. The position of the means for measuring temperature is preferably controlled using an x-y-z translation stage equipped with micrometers with a resolution of 10 $\mu$m. The temperature sensing means should be located a distance above the flame such that it is reasonably certain that the sensing means will always be located above the tip of the flame. Preferably, the temperature sensing means is located approximately 3 cm from the tip of the flame formed when only the auxiliary fuel is being burned.

Preferably, this means for measuring temperature is a thermocouple 20, but any other temperature sensing means, such as optical or radiation pyrometers, could also be used with this invention. The means for measuring the temperature should be as small as possible, so that it detects the temperature at a single point, thereby eliminating the need to average temperatures over a wider area. One suitable thermocouple for use in the invention is a fine gauge (0.002 in. diameter) type R (Pt/Pt-13% Rd) thermocouple (P13R-002, OMEGA Corp.). It is preferred that the thermocouple be shielded with an alumina tube, with the exception of the section 1 cm above the junction. Leaving this section unshielded allows for decreased response time of the thermocouple.

The fuel is delivered to the interior conduit means 11 via the first conduit means 35. The first conduit means 35 is also preferably used to convey the sample whose heat of combustion is to be measured to the burner 1, although it could be introduced by an additional conduit means. The sample is most preferably introduced to the first conduit means 35 through the sampling scheme shown in FIG. 1. This preferred sampling scheme includes a means for containing sample such as a sample loop 23 having a first end 38 and a second end 39. A pair of two-way valves 21, 22 are positioned at the first and second ends, respectively, of the sample loop 23. It should be understood that although FIG. 2 depicts using two two-way valves, other valve means, such as a single multi-port valve, can also be used. Furthermore, while these valves can be operated by any conventional means, including by hand, it is preferred that they be controlled by an air actuated solenoid which is controlled by a computer 37 equipped with a digital output module. A computer 37 or equivalent can collect data as well automate the apparatus such that the valves 21 and 22 are switched to allow a new sample to be burned only when the means for determining the flame height indicates that the flame height in the burner corresponds to the height which occurs when no sample is being burned.

Preferably, the valves 21 and 22 are operated in tandem such that they open and close together. Then, when the valves are in a load position (shown in FIG. 1), the material whose heat of combustion is to be measured will enter valve 21 pass through the sample loop 23 and out valve 22, either returning to the material stream or to be vented. When valves 21 and 22 are switched to the inject position, the first end 38 of sample loop 23 is connected to a first t-fitting 24 and the second end 39 of sample loop 23 is connected to a second t-fitting 29. The first t-fitting 24 is connected to a source of auxiliary fuel 50 via conduit means 30, and the second t-fitting 29 leads to the burner via conduit means 34. Another conduit means 33 connects the two t-fittings directly, forming a parallel circuit such that when the valves 21 and 22 are in the second position, some of the fuel will travel through the sample loop 23 and some of the auxiliary fuel will simultaneously travel through the conduit means 33. This parallel path allows for some auxiliary fuel to be continually supplied to the burner so that the flame will be more likely to be maintained even when the sample is not combustible.

The proportion of fuel which travels through the sample loop 23 when the valves 21 and 22 are in the second position is dependent on the relative resistance of the path formed by conduit means 31, 32, the valves 21, 22 and the sample loop 23 versus the resistance of the path formed by conduit means 33. Thus, the proportion of fuel which travels through the sample loop (and therefore the concentration of the sample within the stream of fuel) can be optimized by altering the resistance of either sample loop 23 or conduit means 31, 32 or 33. The flow of fuel should be optimized to allow for the greatest concentration of sample while ensuring that the flame will be maintained even if the sample is incombustible.

As shown in FIG. 1, the calorimeter can also include a secondary mixing means 25 for further dispersing the sample whose heat of combustion is to be measured within the stream of auxiliary fuel. This secondary mixing means 25 can be a section of wider diameter tubing filled with a honeycomb lattice. Any other arrangement which causes turbulent flow so that the sample and auxiliary fuel are sufficiently mixed can also be used. Although generally found not to be necessary, the use of the secondary mixing means 25 may assist preventing the flame from being extinguished when the sample is not combustible by ensuring that auxiliary fuel is always being burned.

The system may also optionally include a second fuel delivery/sampling scheme (not shown). This second fuel delivery/sampling scheme can be substantially identical to the first scheme. This second network can enter the burner through an optional two way valve which could be located at fitting 15 shown in FIG. 1. A second network would allow one sample to be be burned while another sample is being loaded into a sample loop, thus decreasing the time needed between runs.

Oxygen is delivered through the second conduit 36 to the burner 1 through the annular region 17 formed between the inner conduit means 11 and outer conduit means 12. The oxygen supply should be selected based on its consistency. A consistent oxygen source helps assure that any changes in the height of the diffusional flame are due solely to changes in the samples being burned. A preferable oxygen supply is zero air, which is air without any significant water content.

The auxiliary fuel is delivered to the flame via inner conduit means 11 and can be any number of substances. The auxiliary fuel should be readily combustible and capable of being precisely dispensed such that a known flow rate can be maintained. A preferred auxiliary fuel is methane.

Mass flow controllers 26, 46 are preferably used to precisely control the rates at which both the source of oxygen and the fuel are supplied to the burner. These mass flow controllers 26, 46 can be any number of commercially available mass flow controllers, such as the SIDETRAK III TM brand, sold by Sierra Instrument, Inc. By positioning mass flow controller 46, which controls the flow of auxiliary fuel, upstream of the sampling means, as seen in FIG. 1, the flow rate of material to the burner will be constant before and after sample injection.

The flow rates of the oxygen supply and the auxiliary fuel should be adjusted so that the tip of the flame formed when no sample is present is below the top of the outer conduit means 12. Preferably the tip of the flame is about 2 to 4 cm below the top of the outer conduit means 12. This helps to ensure that the tip of the flame will always be located within the outer conduit means 12, even when burning a sample with a very high heat of combustion.

If the sample is in liquid or solid form, then it is preferably vaporized prior to combustion. Vaporization can be accomplished in any number of known ways such as by pyrolysis, boilng or by passing a stream of inert gas over or through a liquid. Boiling a liquid sample is preferred, as this method provides the most concentrated sample. If the sample becomes too dilute, then even drastic differences in the heats of combustion of different samples produce only slight differences in the flame height, which may be difficult to measure.

It should be realized by one of ordinary skill in the art that the invention is not limited to the exact configuration or methods illustrated above, but that various changes and modifications may be made without departing from the spirit and scope of the invention as described within the following claims.

What is claimed is:

1. An apparatus suitable for use in determining the heat of combustion of a material comprising:
   (a) a burner means capable of producing a diffusional flame;
   (b) a means for conveying a sample of the material to the burner means, so that the sample is burned within the diffusional flame; and
   (c) a means for determining the height of the diffusional flame in the burner means; and
   (d) a means for determining the heat of combustion of the sample by correlating the heat of combustion with the height of the diffusional flame.

2. The apparatus of claim 1 wherein the means for determining the height of the diffusional flame includes a temperature sensing means.

3. The apparatus of claim 2 wherein the temperature sensing means is fixed at a point located directly above the diffusional flame.

4. The apparatus of claim 3 wherein the temperature sensing means comprises a thermocouple.

5. The apparatus of claim 3 wherein the means for determining the heat of combustion of the sample further comprises a microprocessor which directly correlates the temperature at the fixed point with the heat of combustion of the sample.

6. The apparatus of claim 1 wherein the burner means comprises an outer tube means with an inner tube means concentrically located within the outer tube means; a means for conveying fuel and the means for conveying a sample being in fluid communication with the inner tube means; and a means for conveying oxygen connected to the outer tube means such that oxygen can flow in the annular region formed between the inner tube means and the outer tube means.

7. The apparatus of claim 1 wherein the means for conveying a sample to the burner means comprises a valve means and a means for containing sample, wherein the valve means can alternate between a first position which allows sample to flow through the means for connecting the sample without directing the sample to the burner means, and a second position which allows fuel to flow through the means for containing the sample, such that the sample can be loaded into the means for containing sample when the valve is in the first position, and carried to the burner means by the flow of fuel when the valve means is in the second position.

8. The apparatus of claims 7 further comprising a means for mixing the fuel and the sample together before the sample enters the burner means.

9. The apparatus of claim 7 wherein the valve means comprises two two-way valves.

10. The apparatus of claim 9 wherein the two-way valves and the means for containing the sample are configured such that when the valves are in the second position, fuel will simultaneously travel through the means for containing the sample and along a path parallel (in a circuit sense) to the means for containing the sample to the burner means.

11. The apparatus of claim 10 wherein the burner means comprises an outer tube means with an inner tube means concentrically located within the outer tube means; a means for conveying fuel and the means for conveying sample connected to the inner tube means; and a means for conveying oxygen connected to the outer tube means such that oxygen can flow in the annular region formed between the inner tube means and the outer tube means.

12. The apparatus of claim 11 wherein the means for conveying the oxygen and the means for conveying fuel include mass flow controllers.

13. A method for determining the heat of combustion of a material comprising:
(a) forming a diffusional flame;
(b) burning a sample of the material within the diffusional flame;
(c) determining the height of the diffusional flame as the sample is burned; and
(d) determining the heat of combustion of the sample by comparing the height of the diffusional flame determined in step (c) with height of the diffusional flame when a standard sample having a known heat of combustion was burned, the standard having a known value for its heat of combustion.

14. The method of claim 13 wherein determining the height of the diffusional flame includes the step of measuring the temperature at a fixed point above the diffusional flame.

15. The method of claim 13 wherein the diffusional flame is formed by burning an auxiliary fuel, and wherein the auxiliary fuel flows in a stream along a first pathway from a source of auxiliary fuel to the diffusional flame.

16. The method of claim 15 wherein the sample is mixed with the stream of auxiliary fuel prior to being burned.

17. The method of claim 16 wherein the auxiliary fuel is methane.

18. The method of claim 16 wherein the process of mixing the sample with the stream of auxiliary fuel comprises the following steps:
(e) introducing the sample into a segment of conduit which can intermittently be placed in fluid communication with the stream of auxiliary fuel;
(f) placing the segment of conduit in fluid communication with the stream of auxiliary fuel such that as the stream of auxiliary fuel is directed from the source to the diffusional flame, it will carry the sample towards the flame; and
(g) allowing the sample and the auxiliary fuel to mix as the sample travels to the diffusional flame.

19. The method of claim 18 wherein the segment of conduit is intermittently placed in fluid communication with the stream of auxiliary fuel such that the segment of conduit forms a second pathway for the stream of auxiliary fuel, such that the auxiliary fuel will travel through both pathways simultaneously.

20. An apparatus suitable for determining the heat of combustion of a material comprising:
(a) a burner means
(b) a means for conveying a fuel to the burner means;
(c) a means for conveying a source of oxygen to the burner means, the means for conveying fuel and the means for conveying oxygen being arranged so that a diffusional flame will be produced when the fuel is ignited;
(d) a means for conveying a sample of the material to the burner means so that the sample may be burned within the diffusional flame; and
(e) a means for determining the height of the diffusional flame; and
(f) a means for determining the heat of combustion of the sample by correlating the heat of combustion with the height of the diffusional flame.

* * * * *